US006072880A

United States Patent [19]
Shipps et al.

[11] Patent Number: 6,072,880

[45] Date of Patent: Jun. 6, 2000

[54] MODULAR ACTIVE SILENCER WITH PORT DISH

[75] Inventors: J. Clay Shipps, Catonsville; Charles J. Renz, Silver Spring, both of Md.

[73] Assignee: Tenneco Automotive Inc., Lake Forest, Ill.

[21] Appl. No.: 09/032,326

[22] Filed: Feb. 27, 1998

[51] Int. Cl.[7] .......................... H03B 29/00; A61F 11/06; F01N 7/08

[52] U.S. Cl. ........................ 381/71.5; 381/71.3; 181/206; 181/224; 181/228; 248/73; 248/74.3; 248/505

[58] Field of Search ................................ 381/71.5, 71.1, 381/71.3, 71.4, 71.7, 71.8, 86, 94.1, 94.7, FOR 123, FOR 124; 181/227, 228, 229, 224, 222, 206, 202, 198, 217; 415/119; 248/73, 74.1, 74.3, 74.4, 218.4, 219.4, 229.17, 565

[56] References Cited

U.S. PATENT DOCUMENTS

| | | | |
|---|---|---|---|
| 3,712,412 | 1/1973 | Hassett et al. . | |
| 4,133,975 | 1/1979 | Barker, III . | |
| 4,638,965 | 1/1987 | De Bruine et al. | 248/59 |
| 4,643,458 | 2/1987 | Ammar | 285/62 |
| 4,701,951 | 10/1987 | Kash . | |
| 4,939,703 | 7/1990 | Muller . | |
| 5,044,464 | 9/1991 | Bremigan | 381/71.5 |
| 5,194,700 | 3/1993 | Lin . | |
| 5,215,281 | 6/1993 | Sherman | 248/74.1 |
| 5,216,209 | 6/1993 | Holdaway . | |
| 5,229,556 | 7/1993 | Gedes | 181/206 |
| 5,250,763 | 10/1993 | Brown . | |
| 5,272,286 | 12/1993 | Cain et al. | 381/71.7 |
| 5,325,438 | 6/1994 | Browning et al. | 181/204 |
| 5,336,856 | 8/1994 | Krider et al. | 181/206 |
| 5,359,662 | 10/1994 | Yuan et al. . | |
| 5,410,605 | 4/1995 | Sawada et al. . | |
| 5,410,607 | 4/1995 | Mason et al. | 381/71.3 |
| 5,414,230 | 5/1995 | Nieuwendijk et al. | 181/206 |
| 5,440,641 | 8/1995 | Kuusama . | |
| 5,448,645 | 9/1995 | Guerci . | |
| 5,455,779 | 10/1995 | Sato et al. . | |
| 5,466,899 | 11/1995 | Geisenberger . | |
| 5,511,127 | 4/1996 | Warnaka . | |
| 5,541,373 | 7/1996 | Cheng | 381/71.5 |
| 5,546,467 | 8/1996 | Denenberg . | |
| 5,600,106 | 2/1997 | Langley | 181/206 |
| 5,636,287 | 6/1997 | Kubli et al. . | |
| 5,649,685 | 7/1997 | Keller | 248/638 |
| 5,693,918 | 12/1997 | Bremigan et al. | 381/71.5 |
| 5,703,337 | 12/1997 | Geisenberger . | |
| 5,748,749 | 5/1998 | Miller et al. | 381/71.5 |
| 5,799,096 | 8/1998 | Liao | 381/361 |
| 5,828,759 | 10/1998 | Everingham | 381/71.5 |
| 5,848,168 | 12/1998 | Shipps et al. | 381/71.7 |
| 5,873,429 | 2/1999 | Qutub | 248/59 |
| 5,890,685 | 4/1999 | Takahashi | 248/74.3 |
| 5,908,187 | 6/1999 | Kalkoske et al. | 248/635 |

FOREIGN PATENT DOCUMENTS

| | | | |
|---|---|---|---|
| 6-101444 | 4/1994 | Japan | 181/228 |

*Primary Examiner*—Forester W. Isen
*Attorney, Agent, or Firm*—Harness, Dickey & Pierce, P.L.C.

[57] ABSTRACT

A modular Active Noise Control exhaust silencing system is provided including a housing defining an acoustic enclosure having an acoustic outlet port. A speaker is disposed within the acoustic enclosure and an amplifier is disposed within the housing and connected to the speaker. A microphone is associated with the housing for detecting the exhaust noise. A control unit is disposed within the housing in communication with the microphone for receiving signals therefrom. The control unit determines an anti-noise signal for the amplifier for creating an anti-noise responsive to a detected noise source. A port dish is disposed adjacent to the acoustic outlet port which serves as a noise cancellation aid.

35 Claims, 8 Drawing Sheets

MODULAR ACTIVE SILENCER WITH PORT DISH

FIELD OF THE INVENTION

The present invention relates to active noise cancellation systems and more particularly, to a modular exhaust silencing system and a port dish design which enhances noise cancellation.

BACKGROUND OF THE INVENTION

The application of active noise cancellation technology to eliminate various noise signals is generally known within the electronics art. Active noise cancellation is a method of reducing noise by locating, next to a noise source, a second noise source that is equal in amplitude, but 180 degrees out of phase with the noise source. The second source is typically called the "anti-noise" source.

Active Noise Cancellation (ANC) exhaust silencing systems typically use one or more speakers, an acoustic enclosure, a microphone, a Digital Signal Processor (DSP) controller, amplifiers to drive the speakers, a power supply, and a synchronous signal. The microphone is mounted near the noise and anti-noise sources and measures the acoustic levels. The synchronous signal is usually derived from an existing speed sensor mounted on the moving machinery or from a sensor which is installed on the machinery. The controller reads the microphone and synchronous sensor inputs and calculates the anti-noise required to cancel the noise. The controller sends the signal to the amplifier which amplifies the noise to the appropriate level and broadcasts the noise through the speakers mounted in the acoustic enclosure. The enclosure has an opening called a port through which the noise is radiated into the atmosphere. This process is repeated continuously by the controller for optimum noise cancellation.

The acoustic enclosure can be designed to produce a large amount of sound over a narrow frequency rage. This type of design is commonly called a fourth order band pass enclosure. The primary enclosure parameters which determine the operational frequency range and the amount of sound produced are the speaker, back volume, front volume, and the port area and length. The back volume is the air enclosed behind the speaker. The front volume is the air in front of the speaker and in contact with the port. The port is the opening that separates the front volume of air from the outside environment. By varying the values and ratios of these parameters, the sound level and bandwidth of the enclosure can be altered to meet the output requirements dictated by the noise source.

The scope of this disclosure primarily covers the application of ANC exhaust silencing systems to the exhausts of large stationary engines and positive displacement blowers. However, these inventions can be used for other exhaust applications such as vehicular, heavy duty, farm equipment, and marine exhausts.

In the past, there was a tendency to have a different enclosure design for each different exhaust pipe size. The exhaust pipe sizes generally range from 3 inches in diameter to 24 inches in diameter. The smaller engines with small exhausts pipes were generally less noisy and only needed one or two speakers and small enclosures to create the appropriate "anti-noise." The larger engines with large exhausts pipes were louder and required more speakers and larger enclosures to create sufficient "anti-noise." The exhaust noise of the different engines and blowers is controlled by several factors including the number of cylinders in an engine or the number of lobes in a blower, the typical load under which the engine or blower is operating, and the configuration of the exhaust system. The enclosures were typically designed with one engine or blower configuration in mind.

Another design factor which affected past designs was the incorporation of exhaust flow tubes into the enclosure. The flow tube had a flange mounted on one end which was then mounted to a traditional passive silencer or to the end of the existing exhaust pipe. The enclosure was built around the flow tube and therefore had to compensate for the volume taken up by the flow tube. This caused the enclosures to be large especially in the case of large flow tube diameters. The incorporation of the flow tube also caused the enclosure to be heated up by the radiation of heat from the tube. To reduce this heating effect, a heat shield was placed around the flow tube to serve as an insulator. This feature further caused the designs to increase in size.

Due to the different pipe sizes and the above constraints, the past exhaust silencing products were all very different. Using the same basic concepts in their designs, the prior designs all combine multiple speakers with specific acoustic parameters to achieve the desired amount of sound level required for noise cancellation on a designated exhaust pipe size. The 3-inch system typically uses two 8-inch speakers and the 10-inch and 22-inch systems typically use three 12-inch speakers to generate the anti-noise. The electronics required for the above systems were housed in a separate electrical box which is located away from the acoustic enclosure.

Though the current active noise cancellation systems of this type worked well, there were still several shortcomings. For example, the many different engine and blower pipe sizes and thermal differences required several different products to cover the desired market. Each product was completely different and all designs utilized only a few common parts. The existing systems which incorporate the flow tube, flange, and heat shield into the acoustic enclosure are very large. The size of the systems obviously increased with the size of the exhaust pipe. The past mufflers were made of welded sheet steel, the flow tubes were schedule 40 steel pipe, and the flanges were also steel. All of these factors caused the product to be very heavy.

Due to the large size and weight of the acoustic enclosures, the installation of the system was very difficult and required several individuals and/or heavy equipment. The cost of this equipment was the responsibility of the customer. Also, in most cases an additional flange had to be attached to the existing exhaust pipe to allow for mounting of the enclosure. Due to the large amount of extra weight placed at the ends of the exhaust pipes, extra braces often had to be installed to support the pipes or the enclosure.

Most of the exhaust silencing systems were designed for worst case (i.e. loudest exhaust noise applications) situations. Therefore, for most applications, the systems could generate much more anti-noise than was necessary for adequate noise attenuation. In some cases, the three speakers and three amplifiers along with a great deal of acoustic volume were often doing the same job that could have been accomplished with just two speakers, two amplifiers and less volume.

The past systems separated the electronics into separate boxes which were mounted at a remote location. The amplifiers, controllers, and power supplies were mounted inside these boxes. Since the enclosures were mounted apart from the electronics, the amount of cable needed was significant. There were up to three sets of speaker wire and one microphone cable. The microphone cable had to be shielded, due to the relatively low level of the microphone signal, to prevent electromagnetic corruption. It is also a common practice to keep the amount of speaker wire between the amplifier and the speaker to a minimum to prevent signal losses in long lengths of wire. The past systems violated this practice for most applications.

All of the reasons listed above contributed to the high cost of the past product. Due to the large sizes and high piece costs of the past product, it was difficult to order large quantities of any of the products. Uncertainty in the market made it difficult to know how many of each size to keep in stock. Therefore, most had to be built on demand which caused delays in delivery. The low volume builds caused the piece price to be high due to manufacturing scheduling issues and material purchases. The past products also required a great deal of welding and machining. These tasks required a great deal of very skilled labor which further added to the cost.

One method of aiding noise cancellation in the past was to use a device sometimes called a "mixing chamber." A simplified description of a mixing chamber is a box attached to the noise and anti-noise outlets. The box is closed around the two outlets and open to the atmosphere on the opposite end. The end of the box which is open to the atmosphere is generally larger than either the noise or the anti-noise outlets. The mixing chamber varies in noise/anti-noise configuration.

For the concentric configuration of past ANC products, the presence of the mixing chamber resulted in two effects. First, the chamber caused the anti-noise and exhaust noise sources to radiate more efficiently thereby increasing the output of each source. The mixing chamber was behaving similar to an acoustic horn by decreasing the impedance mismatch at the point where the source radiates into the atmosphere. Secondly, the chamber resulted in better cancellation of the noise source as compared to when the mixing chamber was not present.

SUMMARY OF THE INVENTION

The system of the present invention is designed to overcome the shortcomings listed above. Specifically, the present invention provides a system which reduces the need for specialized products for specific applications, sound levels, exhaust pipe sizes, etc. In addition, the system provides an Active Noise Cancellation exhaust silencing system which is reduced in size and weight in comparison with previous systems. The system of the present invention is also much less expensive and much easier to install than the prior art exhaust silencing systems. Furthermore, the system of the present invention can be provided to fit the customer's specific needs without providing an "overkill" system which provides much more noise silencing capability than is required in a specific application. The system of the present invention provides an improved electrical layout which incorporates the amplifier and controller portion of the electronics into the acoustic enclosure. To avoid signal losses over long cable runs, the speaker cable lengths are kept short since the amplifiers are disposed within the housing. The microphone is mounted to the housing in order to keep the voltage level of the microphone signal low in order to avoid additional signal boosting circuitry. Each of the above features of the present invention also contribute to a reduced cost for the present invention in comparison with prior silencer designs.

Accordingly, the system of the present invention provides an Active Noise Cancellation exhaust silencing system including a housing defining an acoustic enclosure having an acoustic outlet port. A speaker is disposed within the acoustic enclosure and an amplifier is disposed within the housing and connected to the speaker. A microphone is mounted to the housing for detecting the exhaust noise. A control unit is disposed within the housing in communication with the microphone for receiving signals therefrom. The control unit determines an anti-noise signal for the amplifier for creating an anti-noise responsive to a detected noise source.

According to another aspect of the present invention, an active noise cancellation exhaust silencing system is provided with a housing defining an acoustic enclosure having an acoustic outlet port. A speaker is disposed within with the acoustic enclosure and an amplifier is connected to the speaker. A port dish is disposed adjacent to the acoustic outlet port which serves as a noise cancellation aid.

Further areas of applicability of the present invention will become apparent from the detailed description provided hereinafter. It should be understood however that the detailed description and specific examples, while indicating preferred embodiments of the invention, are intended for purposes of illustration only, since various changes and modifications within the spirit and scope of the invention will become apparent to those skilled in the art from this detailed description.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
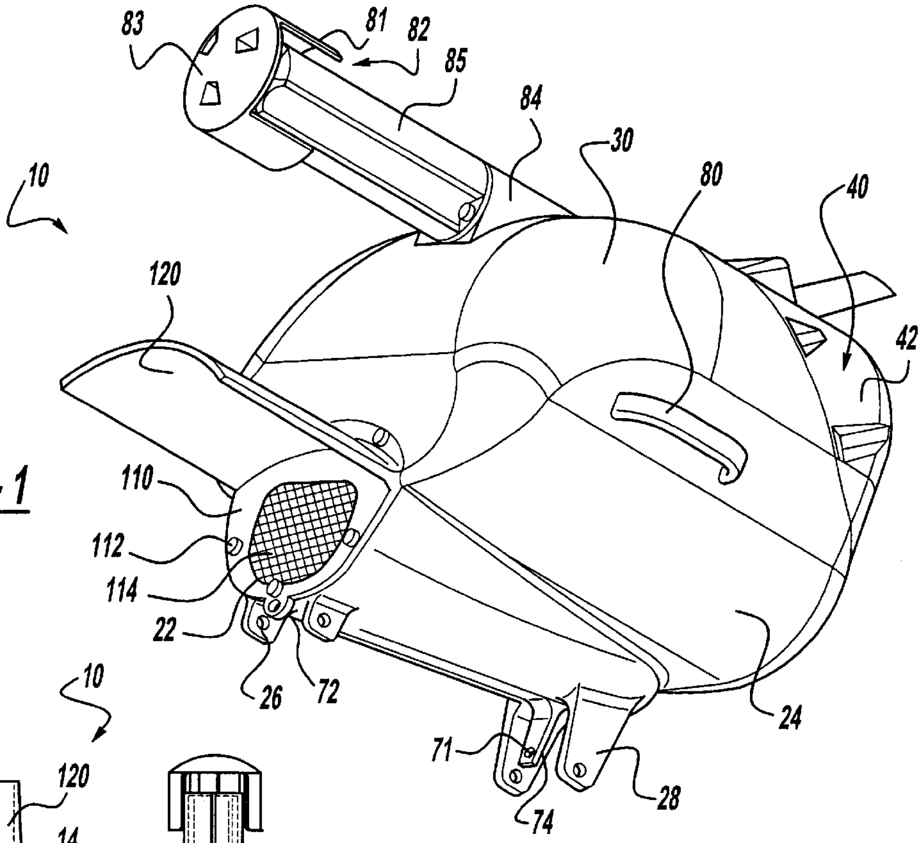
FIG. 1 is a perspective view of a modular active noise silencer according to the principles of the present invention.
Figure 2:
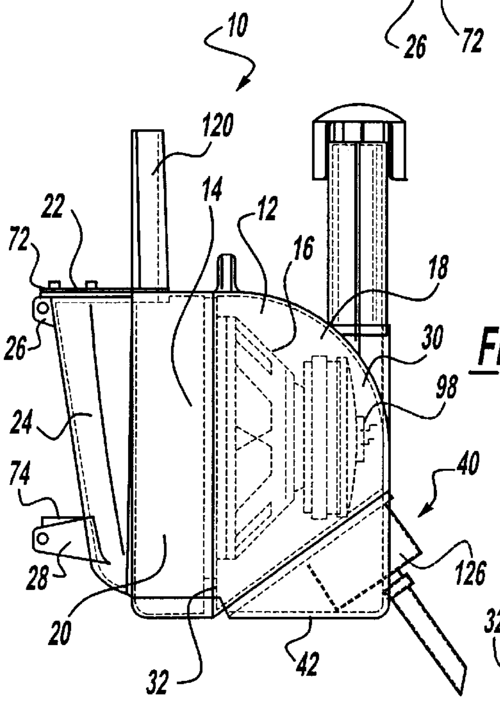
FIG. 2 is a side view of the modular active noise silencer according to the principles of the present invention with the internal components shown in phantom.

With reference to FIGS. 1–7, the modular active noise silencer 10 of the present invention will be described. The modular active noise silencer 10 includes a housing 12 which defines an acoustic enclosure 14, as best shown in FIG. 2. A speaker 16 is provided in the acoustic enclosure 14. The acoustic enclosure 14 is designed to produce a large amount of sound over a narrow frequency range. The acoustic enclosure 14 is of the type commonly referred to as a fourth order band pass enclosure. The primary enclosure parameters which determine the operational frequency range and the amount of sound produced are the speaker 16, back volume 18, front volume 20, and the port 22 area and length. The back volume 18 is the air enclosed behind the speaker, and the front volume 20 is the air in front of the speaker and in contact with the port 22. The port 22 is the opening that separates the front volume of air from the outside environment. By varying the values and ratios of these parameters, the sound level and band width of the enclosure 14 can be altered to meet the output requirements dictated by the noise source.

Figure 3:
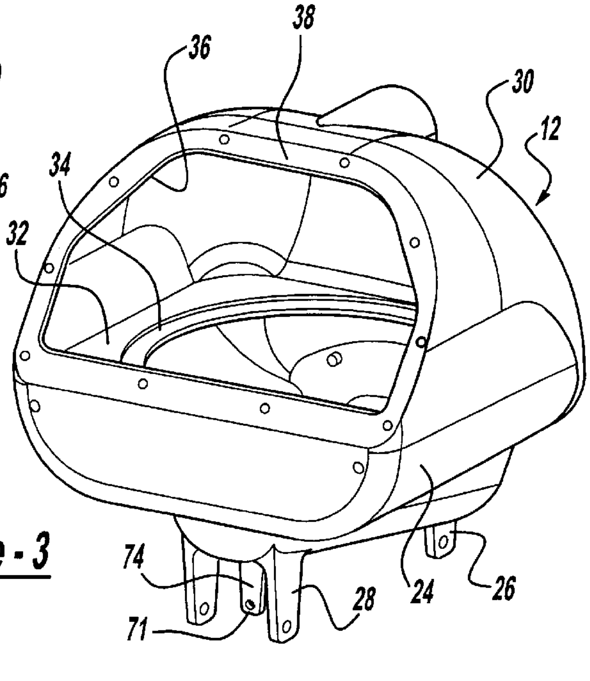
FIG. 3 is a perspective view of the housing of the modular active noise silencer according to the principles of the present invention.

Housing 12 generally includes a first shell portion 24 which is provided with a pair of upper and lower mounting standoffs 26, 28, respectively. Housing 12 also includes a second shell portion 30 which also defines the back volume 18. Preferably, housing 12 is cast as one piece from aluminum. Thus, housing 12 is described as having shell portions 26, 30 for convenience, even though they form a one-piece enclosure. As best seen in FIGS. 2 and 3, a speaker plate 32 is disposed between first and second shell portions 24, 30 and is also preferably cast as an integral part of housing 12 for structural rigidity and to reduce unwanted vibrations. Speaker plate 32 is provided with an annular recess 34 against which the front mounting flange of speaker 16 is seated.

Figure 4:
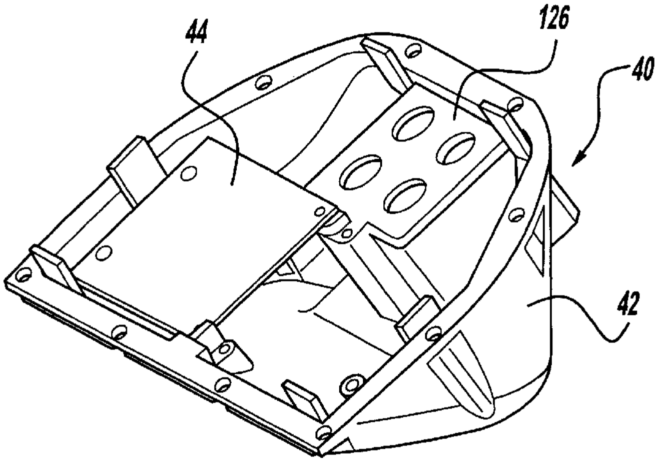
FIG. 4 is a perspective view of the electronics module for containing the amplifier which is mounted to the housing of the modular active noise silencer according to the principles of the present invention.
Figure 5:
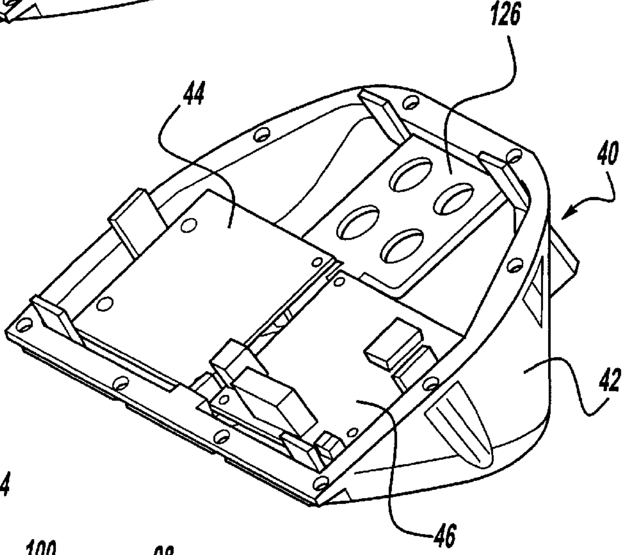
FIG. 5 is a perspective view similar to FIG. 4 with a control unit and amplifier being shown mounted within the electronics module according to the principles of the present invention.
Figure 6:
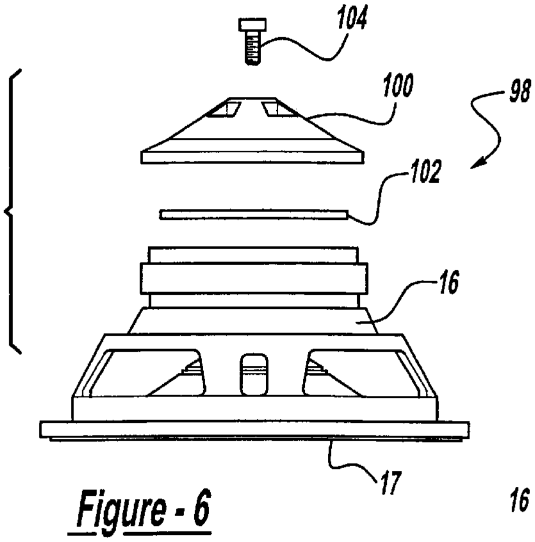
FIG. 6 is a side view of the speaker and corresponding mounting assembly.
Figure 7:
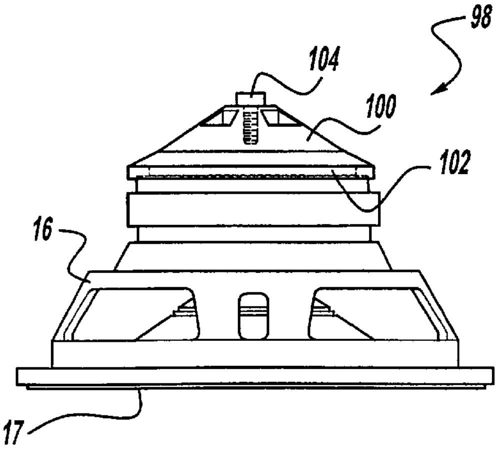
FIG. 7 is a side view of the speaker and mounting assembly in an assembled condition.

The second shell portion 30 of housing 12 includes an opening 36 which is surrounded by a flange 38 which is engaged by an electronics module 40, best shown in FIGS. 4 and 5. Electronics module 40 includes a third shell portion 42 which defines part of housing 12 when installed. Electronics module 36 houses the amplifier printed circuit board 44 as well as the controller printed circuit board 46, shown in FIG. 5. As will be described later, a plurality of modular active noise silencers can be utilized in a single application. In this case, only a single controller 46 is required. Accordingly, with each multiple unit system, there is a master enclosure and the remaining enclosures are slave enclosures. The electronics module 40 of a slave enclosure, shown in FIG. 4, has only an amplifier 44 mounted inside while the master enclosure, shown in FIG. 5, has a controller 46 and an amplifier 44 mounted inside.

Figure 8:
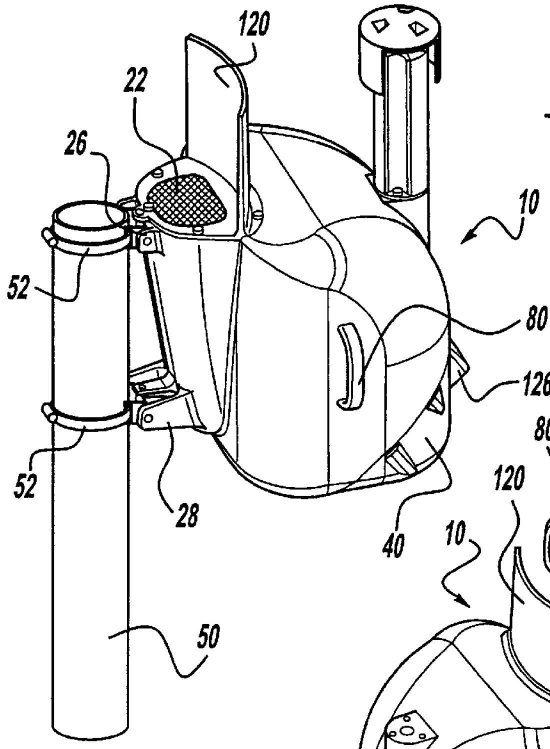
FIG. 8 is a perspective view of a single modular active noise silencer as assembled on a 3-inch exhaust pipe according to the principles of the present invention.
Figure 13:
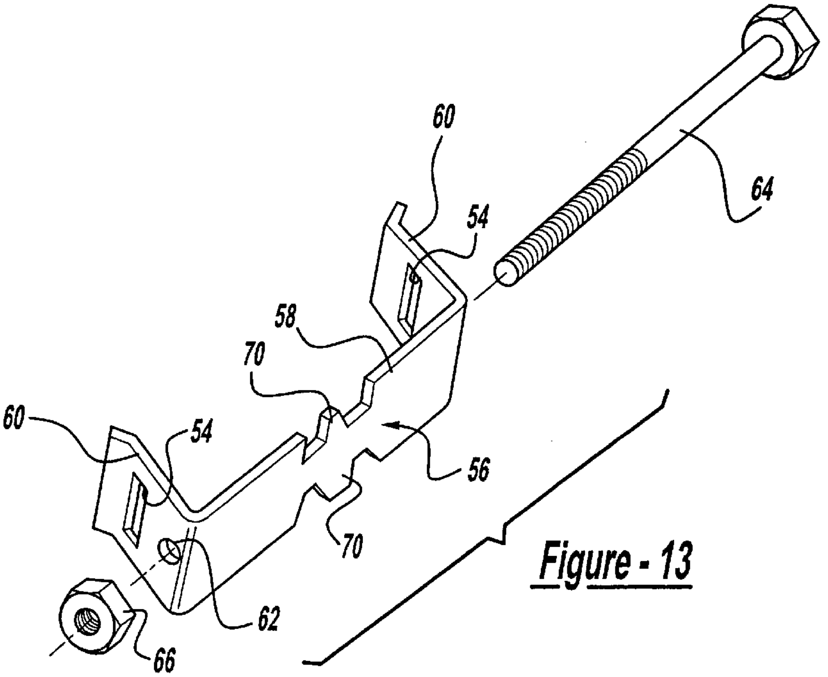
FIG. 13 is an exploded perspective view of the mounting bracket and fastener utilized in conjunction with the band clamps for securely mounting the modular active noise silencers to an exhaust pipe according to the principles of the present invention.

An Active Noise Cancellation exhaust silencing system utilizing a single modular active noise silencer 10 is shown in FIG. 8. The modular active noise silencer 10 is mounted to an exhaust pipe 50. The mounting system for mounting the modular active noise silencer 10 to the exhaust pipe 50 includes a pair of appropriately sized annular bands 52 which wrap around exhaust pipe 50 and which pass through band receiving holes 54 of a mounting bracket 56, as best shown in FIG. 13. With continued reference to FIG. 13, mounting brackets 56 include a body portion 58 having a pair of legs 60 through which band receiving holes 54 are disposed. A pair of bolt holes 62 are provided in each leg 60 for receiving a fastener 64 which secures the upper and lower mounting standoffs 26, 28 to the respective mounting bracket 56. A nut 66 is secured to the fastener 64 for securing the mounting standoffs 26, 28 in place.

Figure 9:
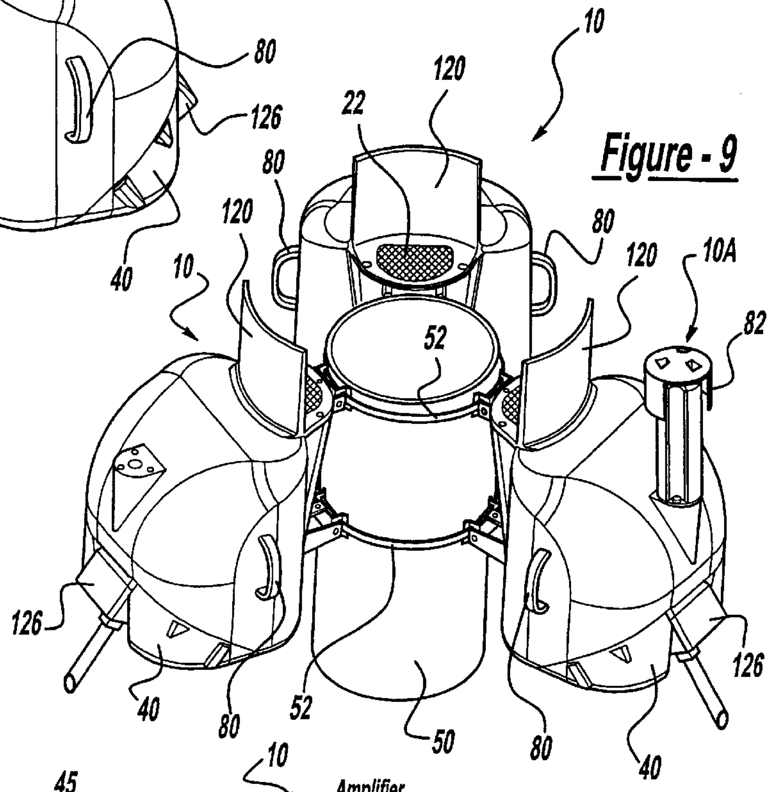
FIG. 9 is a perspective view of three modular active noise silencers as utilized with a 10-inch exhaust pipe, according to the principles of the present invention.
Figure 12:
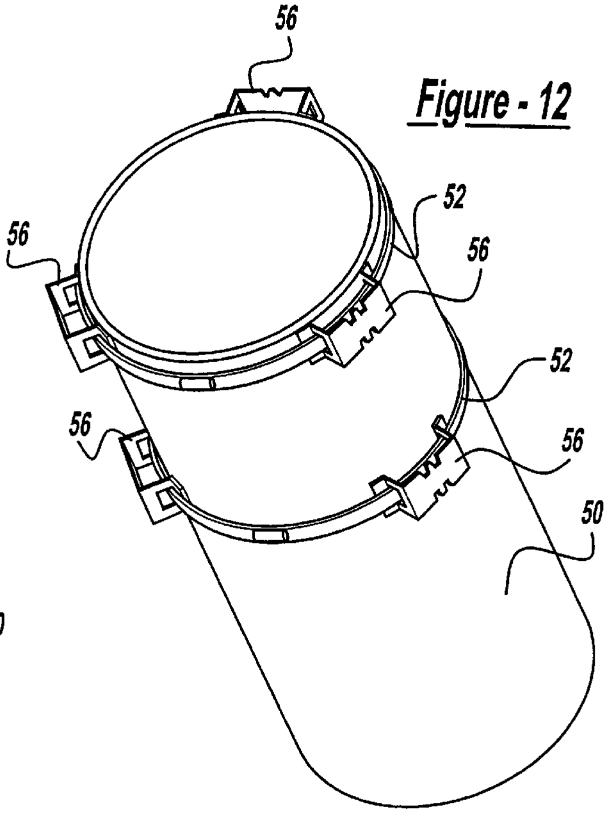
FIG. 12 illustrates an exemplary mounting bracket arranged for use with a 10-inch pipe for supporting three modular active noise silencers as in FIG. 9.

In an Active Noise Cancellation exhaust silencing system which utilizes multiple modular active noise silencers 10, as shown in FIG. 9, a similar mounting system is utilized including a plurality of mounting brackets 56 being disposed on the annular bands 52, as shown in FIGS. 9 and 12. The mounting brackets 56 are provided with centrally located tabs 70, as shown in FIG. 13 which are engaged by an opening 71 in upper and lower support arms 72, 74 which are best shown in FIG. 1. The support arms 72, 74 allow the modular active noise silencer 10 to be hooked into place with the tabs 70 of the mounting brackets 56 temporarily so that the standoffs can be securely mounted to the mounting brackets 56 by fastener 64. The upper and lower support arms 72, 74, along with the tabs 70 of mounting bracket 56 allow for easy installation of the modular active noise silencer 10 to the exhaust pipe 50. In addition, handles 80 may optionally be provided on the housing 12 in order to assist in the installation of the modular active noise silencer 10.

Figure 10:
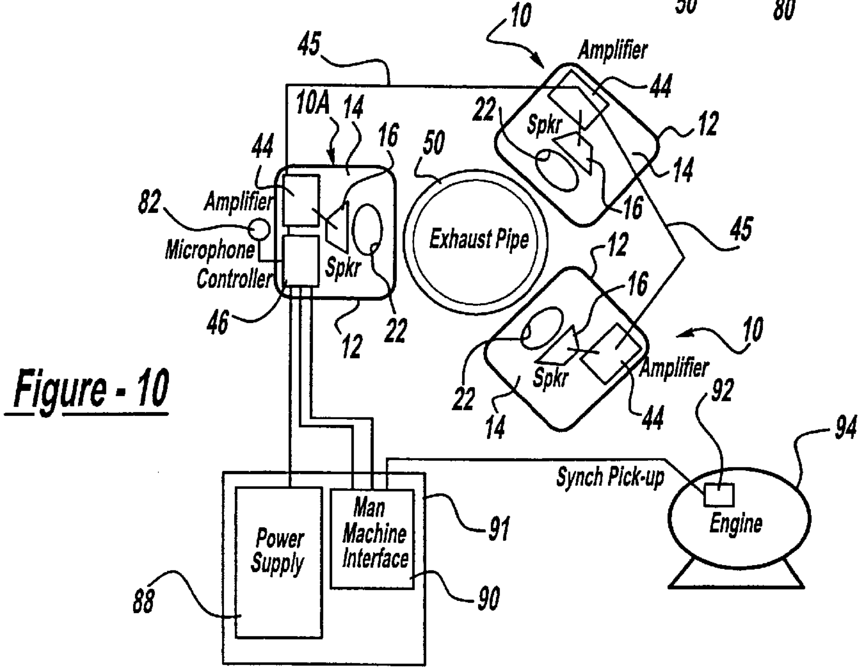
FIG. 10 is a schematic illustration of the system wiring for the active noise cancellation exhaust silencing system of FIG. 9.
Figure 11:
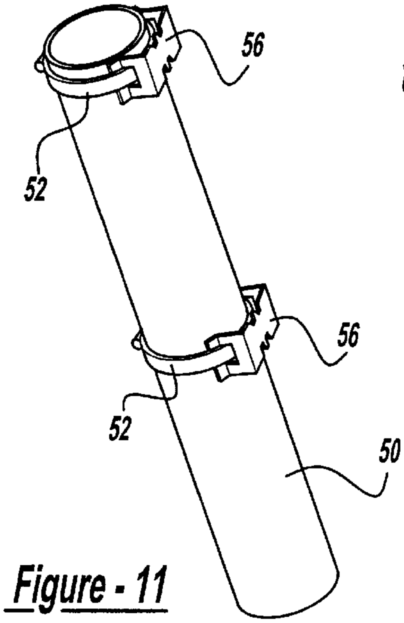
FIG. 11 illustrates an exemplary mounting bracket as assembled on a 3-inch pipe for supporting a modular active noise silencer as shown in FIG. 8.

With reference to FIGS. 1, 9 and 10, a microphone assembly 81 is mounted to the housing 12. Microphone assembly 81 includes a microphone 82 mounted to a stand 85. A cap member 83 is provided over top of the microphone 82 to provide a heat shield and to protect the microphone from snow, ice, rain, and debris. Housing 12 is provided with a microphone mount platform 84. Stand 85 is mounted to the microphone mount platform 84 of housing 12. More than one stand 85 can be stacked on top of each other for adjustably placing the microphone 82 above the plane of the exhaust outlet. Microphone 82 is connected to controller 46 which receives signals from the microphone and provides an anti-noise signal to the amplifier 44 and in response provides a signal to the speaker 16.

As shown in FIG. 10, controller 46 is connected to a power supply 88 and an interface terminal 90 which are preferably located in a separate enclosure 91 positioned away from the modular silencers 10. A synchronous signal is derived from a speed sensor 92 mounted on the engine or other machinery 94. The controller 46 receives the signals produced by microphone 82 and synchronous sensor 92 and calculates the anti-noise required to cancel the noise. The controller 42 sends the anti-noise signal to each of the amplifiers 44 via supply cable 45 which amplify the anti-noise signal to the appropriate level and broadcast the anti-noise signal through the speakers 16 mounted in the acoustic enclosure 14. The noise is radiated from the enclosure 14 through the port 22 into the atmosphere. This process is repeated continuously by the controller 46 for optimum noise cancellation. It should be understood that supply cable 45 includes sufficient connectors and shielding to carry the anti-noise signal and appropriate level of DC power to each amplifier 44.

In an active noise cancellation exhaust silencing system which utilizes multiple modular active noise silencers 10, the controller 46 of the master enclosure 10A sends the signal to each of the amplifiers 44 provided in each of the silencers 10. In an active noise cancellation exhaust silencing system utilizing multiple modular active noise silencers 10, a single microphone 82 is utilized. Preferably, microphone 82 is provided on the master silencer 10A so that the microphone cable connection to the controller 46 can be kept short for eliminating unwanted electrical noise. The electronics module 40 is provided with a junction box 126 for providing connections between the silencers 10, interface terminal 90 and power supply 88. Preferably, interface terminal 90 is a man machine interface as is known in the art.

The speaker 16 is mounted within the acoustic enclosure 14 by a pressure plate assembly 98 as shown in FIG. 2. The pressure plate assembly 98 includes a pressure plate 100 which is pressed against the rearward surface of the speaker 16. An optional thermal conductive material 102 can be provided between the pressure plate 100 and speaker 16. An axial force member, such as a machine screw or bolt 104, is inserted into a threaded bore on a back surface of the pressure plate 100. The speaker 16 is inserted into the acoustic enclosure 14 such that mounting flange 17 of speaker 16 is seated into the annular recess 34 of speaker plate 32. The pressure plate assembly 98 is inserted between the speaker 16 and the interior surface of the second shell portion 30. The bolt 104 is then backed out of the threaded portion in the pressure plate 100 until the head of the bolt 104 engages the wall of second shell portion 30 for providing pressure against the rear surface of the speaker 16 via pressure plate 100, such that the speaker 16 is secured in place.

Port 22 is provided with a removable plate 110 which is mounted to the housing 12. The removable plate 110 is fastened to the housing by a plurality of fasteners 112 and is preferably provided with a screen 114 for preventing debris from entering the acoustic enclosure 14. The removable plate 110 allows the port opening 22 to be easily varied in size by simply replacing the plate 110 with another plate having a larger or smaller port opening 22.

A port dish 120 is provided adjacent to the port 22 and extends away from housing 12. Port dish 120 preferably has a length of seven (7) inches or longer and is generally as wide or wider than the port opening. Port dish 120 is preferably arcuate in shape and is disposed between port 22 and microphone 82 as shown in FIGS. 1 and 2. Port dish 120 acts as a cancellation aid which will be described in greater detail below. Furthermore, port dish 120 provides a heat shield for microphone 82 (where applicable).

The modular active silencer 10 according to the principles of the present invention is a self-contained, multi-functional acoustic enclosure which can be used singularly or in combination on all exhaust pipe sizes for both blower and engine applications. The modular active silencer 10 is designed to achieve maximum acoustic output over a specified frequency range which accounts for the needs of both the blower and engine applications. The silencer 10 is small, lightweight, and uses only one speaker 16 per enclosure which is preferably twelve inches in diameter. For small exhaust pipe applications with low acoustic output, only one silencer may be required for optimum cancellation. However, for larger exhaust pipe applications, where the acoustic output is higher, two or more silencers 10 may be required. The modular feature of the present invention has several advantages over the prior art which are discussed below.

When two or more modular silencers 10 are used together, their outputs, which are virtually identical, add together to create a larger anti-noise signal. This is possible for two reasons:

A. The wavelengths of the cancellation frequencies are very large compared to the acoustic port outlets on the silencers. This allows the silencers to radiate plane waves which means that there is no modal radiation of the port 22.

B. The differences in the distance between each silencer port outlet and the error microphone is small compared to the half wavelength of the frequencies to be cancelled.

Since acoustic output, or Sound Pressure Level (SPL), is measured in decibels (dB) and multiple sound sources are being added together, it is important to understand the appropriate equations. The equation for SPL is $$\text{dB}(SPL)=20*\log(Pm/Pref)$$

where

Pm=measured sound pressure

Pref=reference sound pressure=0.00002 Pa

Since we are adding two noise sources with pressures P1 and P2 we have $$\text{dB}(SPL)_{Total}=20*\log[(P1+P2\ )/Pref]$$

Figure 14:
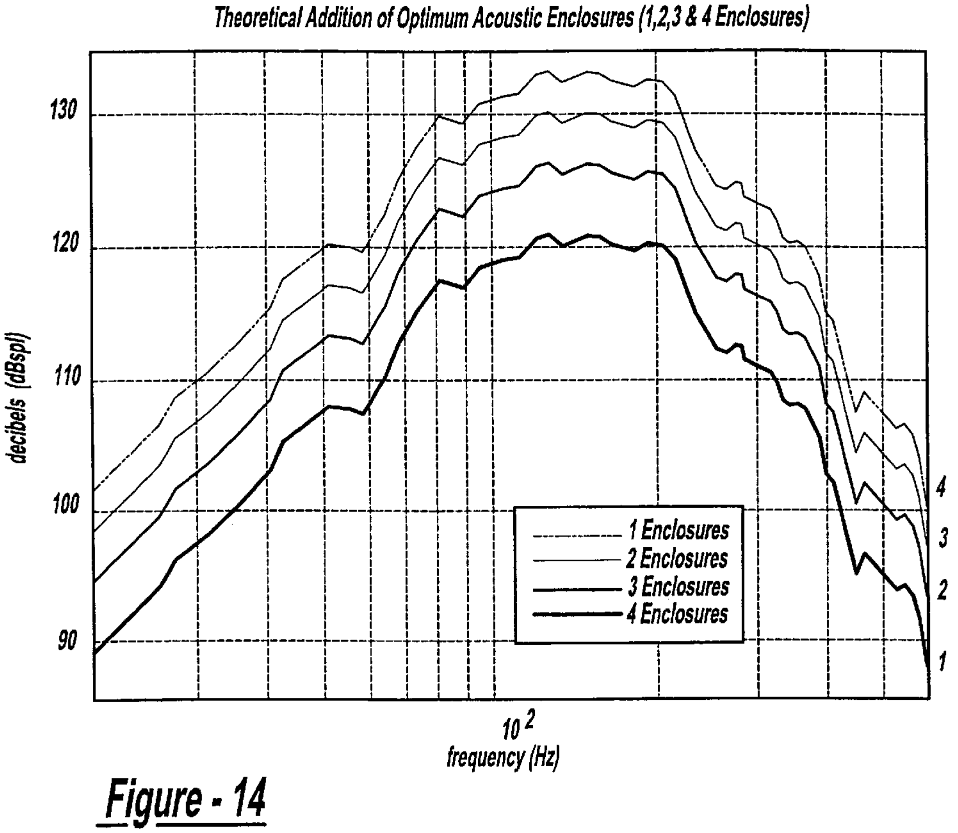
FIG. 14 is a graphical illustration of the sound pressure level increases which result from adding the outputs of multiple acoustic enclosures.
Figure 15:
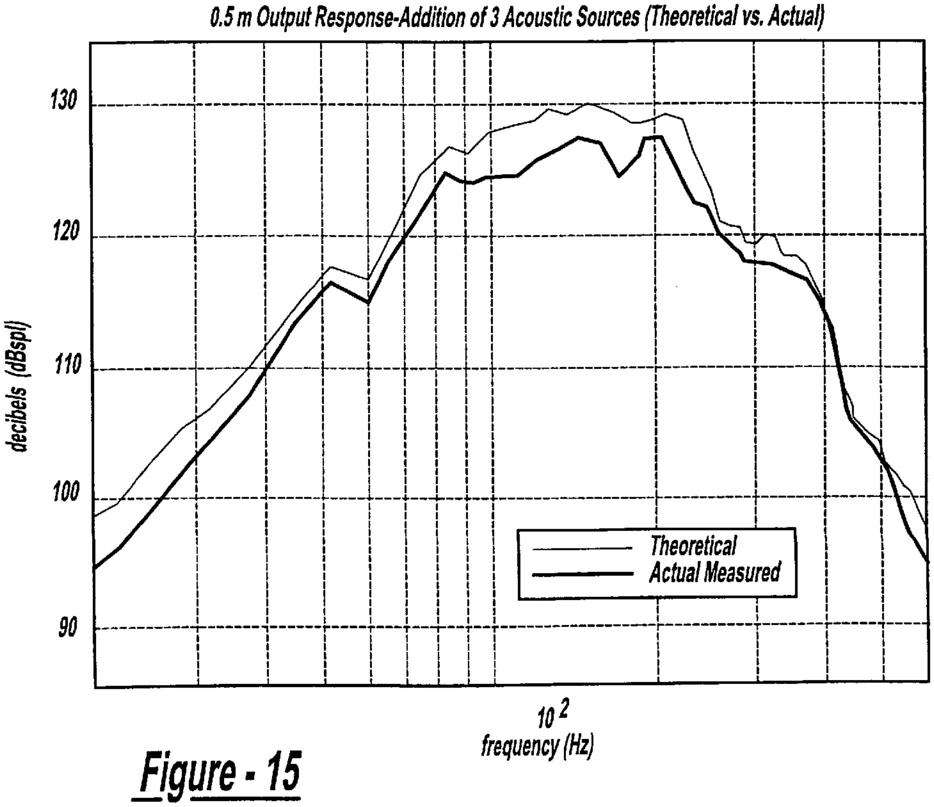
FIG. 15 is a graphical illustration of the theoretical and experimental results of combining the output of multiple enclosures.

If P1 is equal to P2 then we have $$\text{dB}(SPL)_{Total}=20*\log[(2\text{P } 1)/\text{Pref}]$$

which is equivalent to $$\text{dB}(SPL)_{Total}=20*\log[\text{P1}/\ \text{Pref}]+20*\log[2]$$

where 20*log(2) is equal to six dB. So if the noise sources are identical, then the resultant SPL of the combination of "n" units is the SPL of one unit plus 20*log(n). Due to size constraints, however, it will be difficult to use more than four modular silencers 10 around an exhaust pipe so the combinations of two, three, and four silencers will result in SPL increases of six, nine, and twelve dB. FIGS. 14 and 15 show the theoretical and experimental results of adding the outputs of multiple silencers together.

Since the modular silencer acoustic outputs can be added together, each application can be outfitted using the same modular silencer 10 in varying numbers. Therefore, the need for specialized products for specific applications, sound levels, exhaust pipe sizes, etc. is not necessary. This results in a significant cost savings because one or more modular silencers can be used for any number of ANC applications, thereby eliminating the need to custom design an ANC system for the specific application. Also, the chance of sending a system to a customer which is deemed an "overkill" system is greatly reduced. One possible approach would be to send the customer an "underkill" system and if the results were not optimum, to send the customer another modular silencer 10 to increase their performance. This is possible with the modular approach and allows the customer to purchase only as much noise cancellation as they really need. Since the same modular silencer 10 or multiples thereof, can be used for all applications, more silencers 10 can be manufactured at one time in order to receive a lower piece cost. This results in a much lower cost for the product.

The modular silencer 10 is preferably constructed of cast aluminum, instead of welded sheet steel, and weighs approximately forty-five pounds. The smaller design of the silencer 10 allows it to be easily cast out of aluminum and also, if desired, out of magnesium. The weights of the past product designs compared to the new product design are listed in Table 1 below. The three-inch, six-inch, ten-inch, and 22-inch exhaust pipe sizes correspond to one, two, three, and four modular enclosures respectively for the modular silencer system as can be deduced from the weight increase in multiples of forty-five pounds.

TABLE 1

Product Weight Comparison

| | 3" Exhaust Pipe | 6" Exhaust Pipe | 10" Exhaust Pipe | 22" Exhaust Pipe |
|---|---|---|---|---|
| Prior Designs | 27 lb. | 112 lb. | 235 lb. | 628 lb. |
| Present Invention | 45 lb. | 90 lb. | 135 lb. | 180 lb. |

The acoustic volume required for the modular silencers 10 has also been reduced. The modular silencer 10 uses approximately eighteen liters of acoustic volume for its generation of anti-noise. While the acoustic volume does not equate exactly to the volume of the enclosure, it is accurate within a small percentage and is a sufficient comparison point. The true volume of prior designs is much greater than its acoustic volume due to the inclusion of the flow tube, heat shield and flange. Since the exhaust flow tube and heat shields are no longer incorporated into the enclosure design, certain geometrical constraints have been lifted and the acoustic volumes can be designed smaller. A comparison of the acoustic volumes for the old and new products are listed in Table 2 below. The three-inch, six-inch, ten-inch, and 22-inch exhaust pipe sizes correspond to one, two, three, and four modular enclosures, respectively, for the new product as can be deduced from the volume increase in multiples of eighteen liters.

TABLE 2

Product Acoustic Volume Comparison

| | 3" Exhaust Pipe | 6" Exhaust Pipe | 10" Exhaust Pipe | 22" Exhaust Pipe |
|---|---|---|---|---|
| Prior Designs | 17 liters | 40 liters | 97 liters | 260 liters |
| Present Invention | 18 liters | 36 liters | 54 liters | 72 liters |

Both the weight and volume contribute to the cost of the raw materials for manufacturing the product as well as the cost of shipping the product to a customer. Accordingly, a reduction in either or both saves money.

The new modular design allows for a much easier installation when compared to the prior designs. The very simple mounting bracket and band clamp assembly, shown in FIGS. 8–9 and 11–13 is attached firmly to the exhaust pipe. The module or modules are lifted one at a time and set temporarily on the tabs 70 located on the mounting bracket 56 and then secured with a bolt 64 and nut 66. Since each module weights only 45 pounds, a single person can lift and place the module on the mounting bracket 56. In the past, a crane or forklift was needed for all products except those for a three-inch exhaust pipe because of their large size and weight. The costs of this machinery was part of the installation cost born by the customer and therefore had to be considered when the product was purchased.

Another problem which has been reduced is the need for additional exhaust pipe supports typically a pair of large annular pipe flanges which were mated and secured with several fasteners. The prior designs are very heavy and usually require additional bracing of the exhaust pipe to prevent a failure in the pipe. With the present invention, this concern has been eliminated, especially for large exhaust pipe applications because the mounting flanges are no longer necessary.

The electronics required to operate the prior exhaust silencing system were previously housed in a separate electrical enclosure. The present invention incorporates the amplifier and controller portion of the electronics into the acoustic enclosures, one version which is a "master" and one version which is a "slave", as described above.

The master and slave silencers are physically identical except for the additional printed circuit board mounted on the inside, and a microphone mounted on the exterior. A slave silencer can become a master silencer with the addition of these two components. This approach was chosen for several reasons.

A. The master and slave configuration is used to allow for single and multiple silencer applications. A single silencer application has to have a master silencer and a multiple silencer application has one master silencer and at least one slave silencer.

B. Due to the low voltage level of the microphone signal and to avoid additional signal boosting circuitry, the microphone cable length needs to be kept short. For this to occur, the microphone needs to be located in close proximity to the controller.

C. To avoid signal loss over long cable runs the speaker cable lengths need to be kept short. For this reason, it is optimal to locate the amplifiers very close to the speakers. Since the acoustic enclosures are made of cast aluminum they also serve as heat sinks for the electronics mounted inside.

Port Dish

The port dish 120 shown in FIGS. 1 and 2 is a raised, curved panel which is located close to the outlet or port 22 of the acoustic enclosure 14. The port dish 120 serves as a cancellation aid and as a heat shield for the microphone 82. The port dish 120 behaves similarly to a mixing chamber in that it increases the ability of enclosure 14 to cancel the exhaust noise. However, it differs from the mixing chamber known in the art in an important way because it amplifies only the anti-noise source and does not amplify the exhaust noise source.

Figure 16:
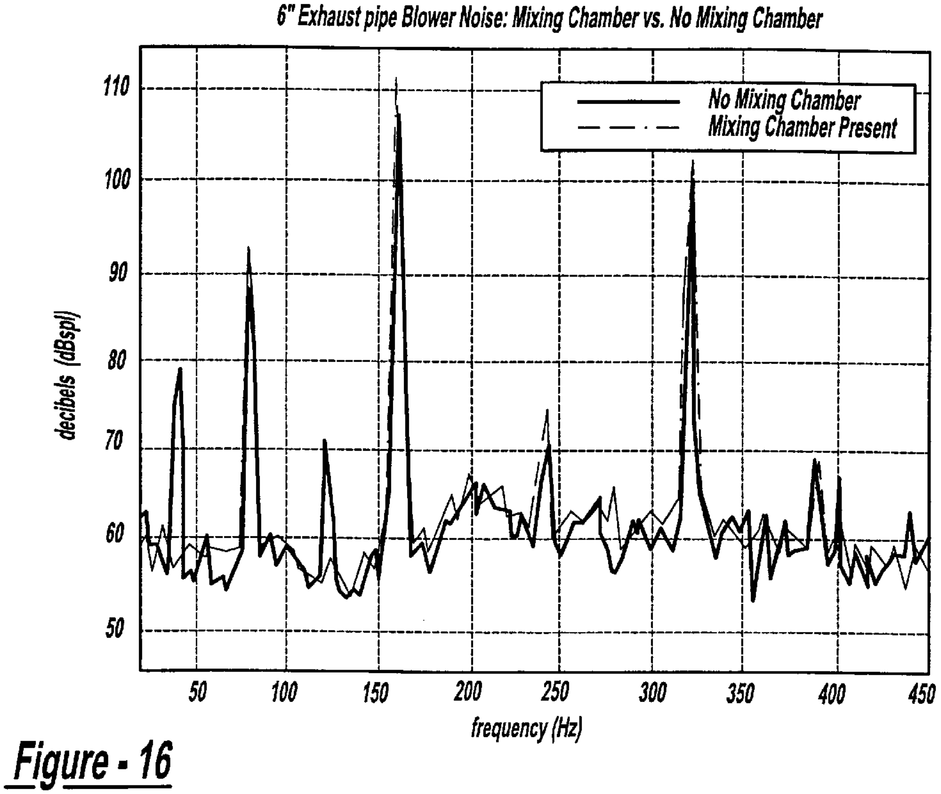
FIG. 16 graphically illustrates the amplification effects of a mixing chamber on noise generated by a 6-inch exhaust pipe versus no mixing chamber.
Figure 17:
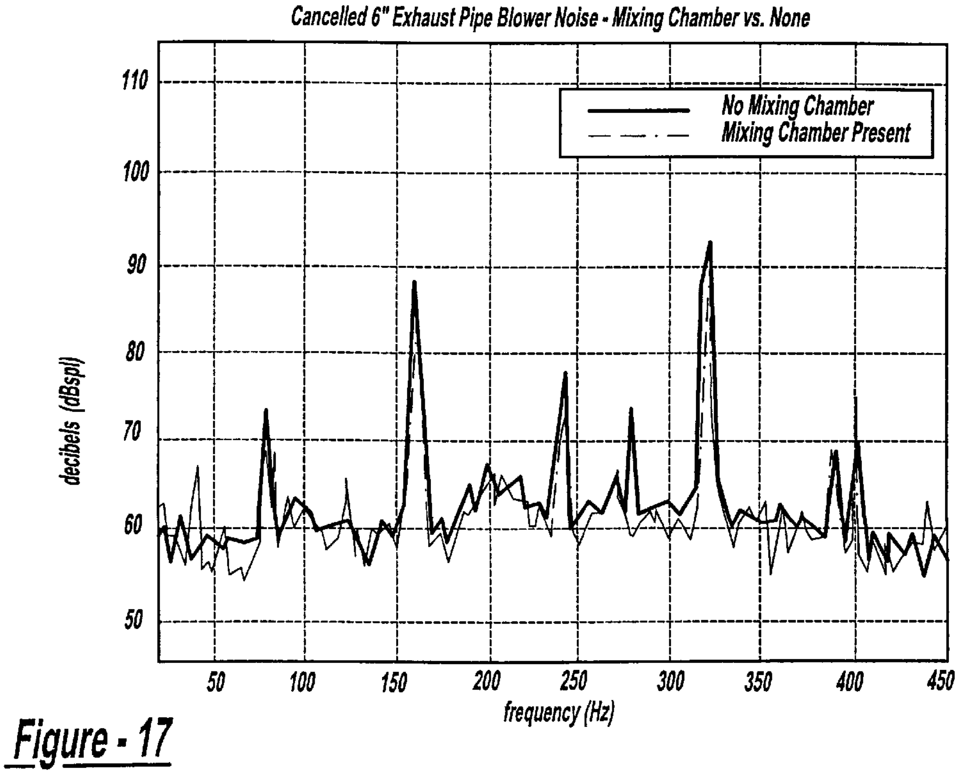
FIG. 17 graphically illustrates the effects of a mixing chamber on noise cancellation in connection with the new modular active noise silencer system without a port dish according to the present invention.
Figure 18:
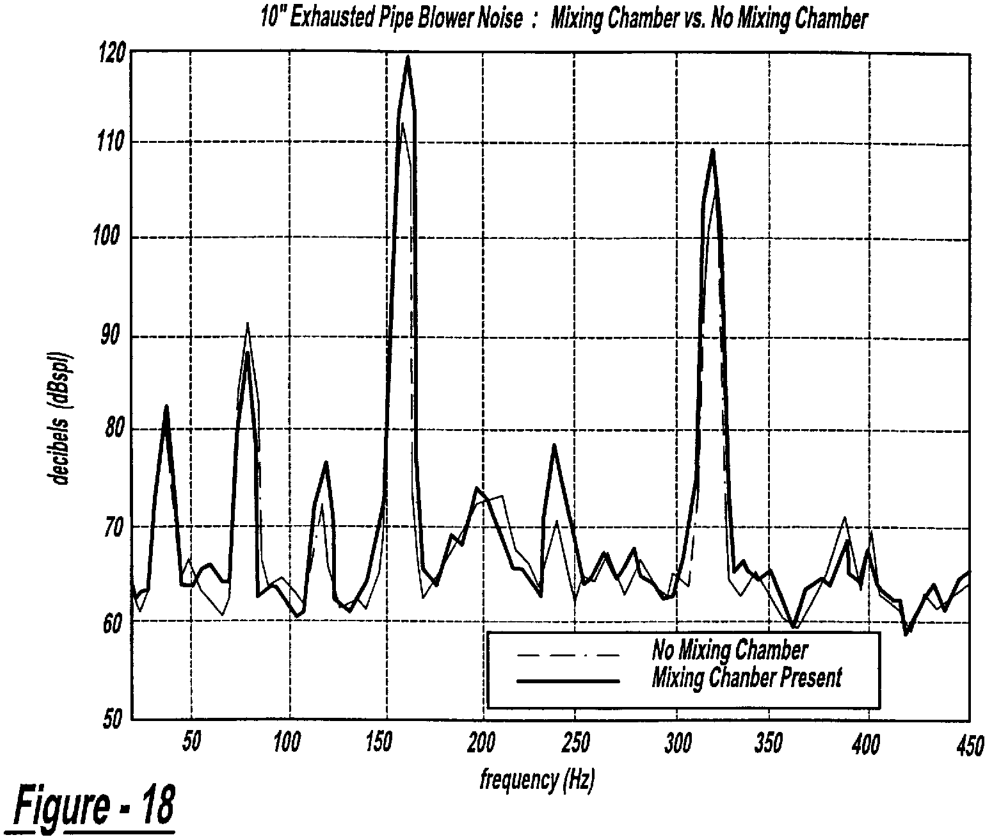
FIG. 18 graphically illustrates the amplification effects of a mixing chamber on a 10-inch exhaust noise versus no mixing chamber.
Figure 19:
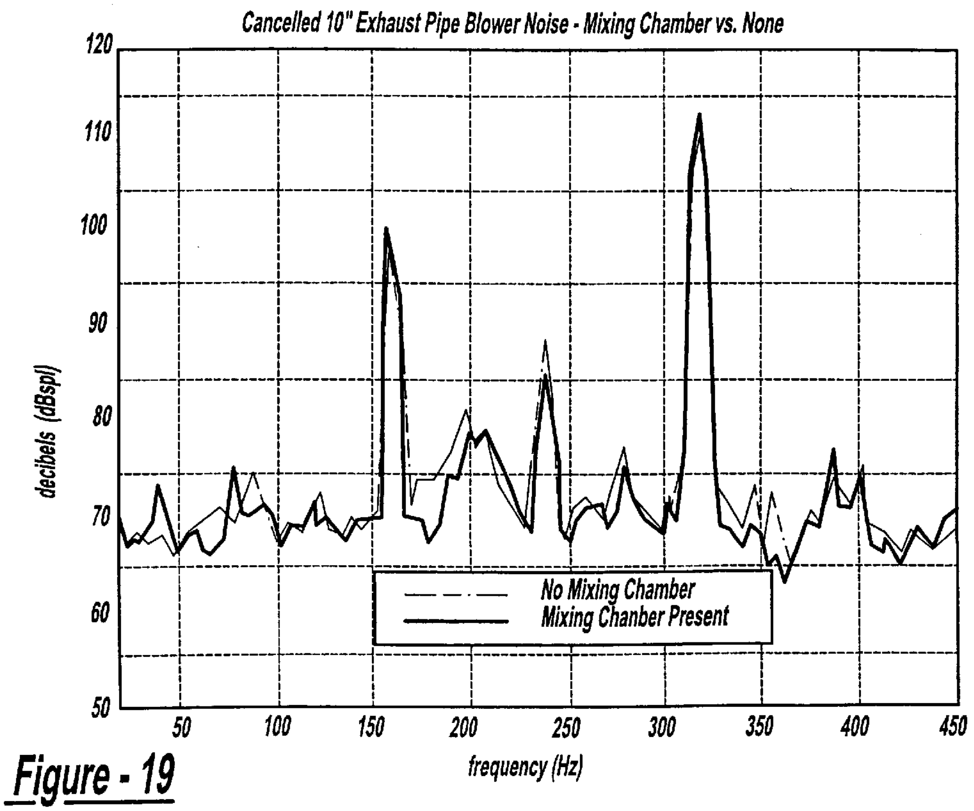
FIG. 19 graphically illustrates the effects of a mixing chamber on cancellation for the modular active noise silencer without a port dish according to the principles of the present invention.

The mixing chamber can cause the exhaust pipe to be a more efficient radiator but have little or no effect on the enclosure's port. This occurs when the diameter of the mixing chamber is very large compared to the diameter of the enclosure's port. To reduce the impedance mismatch between the port and the atmosphere, the transition between the two impedances needs to be gradual. The mixing chamber is the impedance matcher between the port and the atmosphere so it must be a gradual step for the process to be efficient. That is why a horn gradually gets larger in diameter. When a small diameter port radiates into a mixing chamber which is not dramatically larger in diameter then the port is better matched to the impedance of the mixing chamber and thus to the atmosphere. If the port radiates into a mixing chamber which has a diameter that is much larger than the port diameter, then the impedance of the port is not matched well to the impedance of the mixing chamber and therefore will not radiate into the atmosphere as well. The exhaust pipe, however, typically has a diameter which is larger than the diameter of the enclosure's port and is therefore better matched to the large diameter mixing chamber. The result is that the exhaust pipe radiates more efficiently than the small port making it more difficult to cancel the exhaust noise. For this reason, the mixing chamber can be detrimental to cancellation when used on large exhaust pipes with the new modular silencer according to the present invention. FIGS. 16 and 17 show the effects of a mixing chamber on the exhaust noise and cancellation with the new modular ANC system on a six-inch diameter blower exhaust pipe. FIGS. 18 and 19 show the effects of a mixing chamber on the exhaust noise and cancellation with the new modular ANC system on a ten-inch diameter blower exhaust pipe.

In summary, FIGS. 16 and 18 show that the mixing chamber amplified the exhaust noise. Also, FIGS. 17 and 19 show that the mixing chamber acts as a detriment to noise cancellation for the new modular ANC system.

The port dish 120 eliminates this problem because it appears to reduce the impedance mismatch between the enclosures port 22 and the atmosphere but has no effect on the exhaust pipe noise. The enclosure's port 22 then becomes a better radiator of sound while the noise from the exhaust pipe 50 remains unchanged. This is an important effect because the silencer 10 can now cancel more noise with the port dish 22 present than if the port dish 22 were not present, or if there was a mixing chamber in its place.

Figure 20:
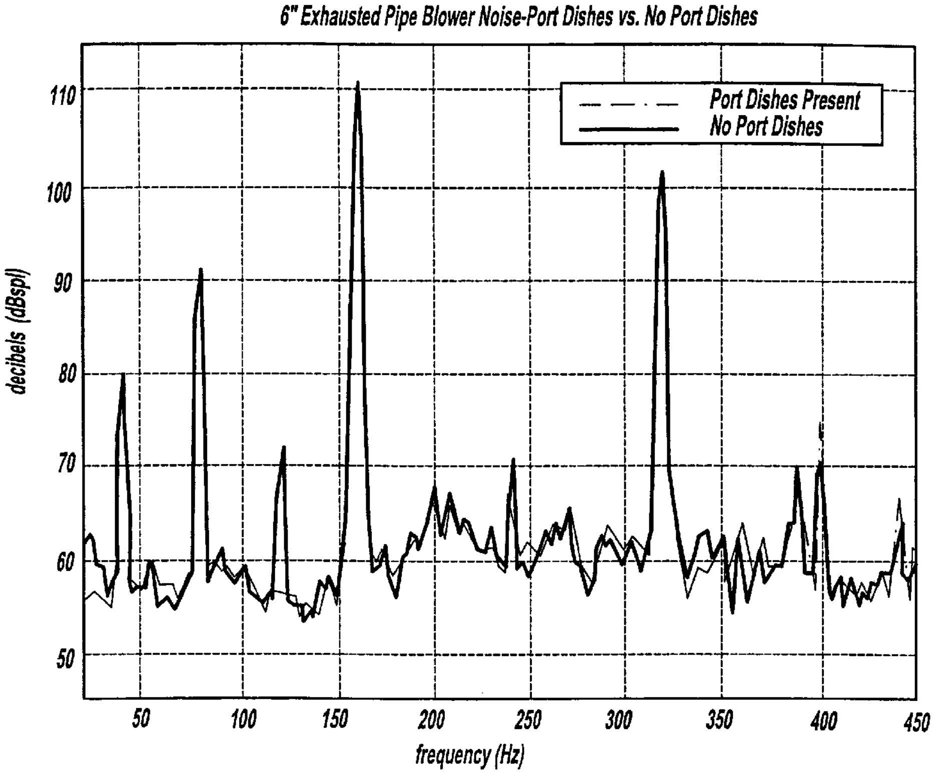
FIG. 20 graphically illustrates the amplification effects of a port dish on noise generated by a 6-inch exhaust pipe.
Figure 21:
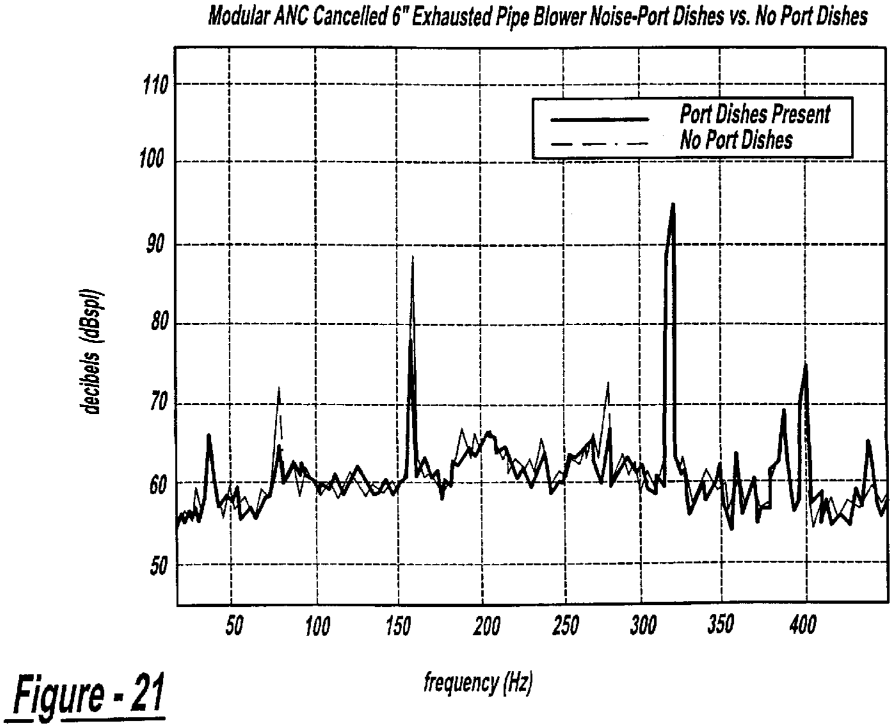
FIG. 21 graphically illustrates the effects of the port dish on cancellation for the modular active noise silencer system of the present invention on a 6-inch exhaust pipe.

In support of this proposition, FIGS. 20 and 21 show the effects of port dishes on the exhaust noise and cancellation with the new modular ANC system on a blower's six-inch diameter exhaust pipe. FIG. 20 shows that the port dishes 22 do not amplify the exhaust noise while FIG. 21 shows that the port dish 22 enhances cancellation for the new modular system.

On several occasions using the prior art silencers, the microphone became charred and dysfunctional due to prolonged exposure to the engine exhaust gases. This occurred because occasionally a prevailing wind would divert the hot exhaust gas from its original path and direct it onto the microphone. This happens mostly when the exhaust gas is not moving at a high rate of speed and therefore can be easily diverted. According to the teachings of the present invention, the placement and height of the port dish 120 and the microphone 82 are such that the microphone 82 will be protected from this phenomena by the port dish 120 and still provide adequate cancellation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An active noise cancellation silencing system, comprising:

a modular housing defining an acoustic enclosure, the modular housing including a body portion and a cover portion, the body portion having a first opening defined by a first mating flange, and the cover portion including a second opening defined by a second mating flange, wherein the first and second mating flanges are similarly dimensioned such that the body portion can receive the cover portion for sealing the acoustic enclosure;

an acoustic outlet port formed in the body portion;

a speaker disposed within the acoustic enclosure;

an amplifier disposed within the cover portion and connected to the speaker;

a microphone mounted to the housing; and a control unit disposed within the cover portion in communication with the microphone for receiving signals therefrom, the control unit determining an anti-noise signal for the amplifier for creating an amplified anti-noise signal responsive to a detected noise source.

2. The silencing system according to claim 1, wherein the cover portion includes a junction box for connecting to an external power source.

3. The silencing system according to claim 1, wherein the body portion is formed from a one-piece aluminum casting.

4. The silencing system according to claim 1, wherein the acoustic enclosure includes a speaker plate disposed therein for supporting the speaker.

5. The silencing system according to claim 4, wherein said speaker plate includes an annular recess for receiving the speaker.

6. The silencing system according to claim 4, further comprising a pressure plate disposed against a rear surface of the speaker and an axial force member operably associated with the pressure plate for applying a force between the pressure plate and an inside surface of the body portion for supporting the speaker in position relative to the speaker plate.

7. The silencing system according to claim 1, further comprising a port dish disposed adjacent to the acoustic outlet port, the port dish positioned partially about a circumference of the acoustic outlet port, the port dish extending perpendicularly from a plane of the acoustic outlet port for reducing the impedance mismatch between the acoustic outlet port and an area surrounding the acoustic outlet port.

8. The silencing system according to claim 7, wherein the port dish is generally arcuate.

9. The silencing system according to claim 7, wherein the port dish is disposed between the acoustic outlet port and the microphone.

10. The silencing system according to claim 1, wherein the microphone is mounted to a stand which is mounted to the housing.

11. The silencing system according to claim 10, further comprising a cap for covering the microphone.

12. The silencing system according to claim 1, wherein the modular housing is mounted on an exhaust pipe.

13. The silencing system according to claim 12, further comprising a mounting assembly secured to an exhaust pipe, the mounting assembly including a mounting bracket and a band clamp for securing the mounting bracket to the exhaust pipe, and a corresponding mounting stand-off formed on the modular housing, the mounting bracket and the mounting stand-off cooperating to support the modular housing on the exhaust pipe.

14. The silencing system according to claim 13, wherein one of the mounting bracket and the mounting stand-off includes a tab and the other of the mounting bracket and the mounting standoff includes a corresponding aperture for receiving the tab for supporting the housing.

15. An active noise cancellation silencing system, comprising:

a plurality of modular silencers radially mounted about the perimeter of an exhaust conduit, each modular silencer including:

a housing having an acoustic outlet port, the acoustic outlet port of each housing being positioned within a plane defined by an opening of the exhaust conduit;

a speaker disposed within the housing;

a port dish disposed adjacent to the acoustic outlet port, the port dish positioned partially about the circumference of the acoustic outlet port, the port dish extending perpendicularly from a plane of the acoustic outlet port for reducing the impedance mismatch between the acoustic outlet port and an area surrounding the acoustic outlet port; and an amplifier disposed within the housing and connected to the speaker;

one of the modular silencers being a master unit including a microphone supported by the housing and a control unit disposed within the housing in communication with the microphone for receiving signals therefrom, the control unit determining an anti-noise signal which is provided to the amplifier of each modular silencer for creating an anti-noise responsive to a detected noise source radiating from the exhaust conduit.

16. The silencing system according to claim 15, wherein each housing includes an electronics module which is detachable from the acoustic enclosure, the amplifier being disposed on the electronics module.

17. The silencing system according to claim 16, wherein the electronics module includes a junction box for providing electrical communication connections between the modular silencers.

18. The silencing system according to claim 15, wherein each of the acoustic enclosures includes a speaker plate disposed therein for supporting the speaker.

19. The silencing system according to claim 15, wherein the port dish is generally arcuate.

20. An active noise cancellation silencing system, comprising:

a housing defining an acoustic enclosure having an acoustic outlet port;

a speaker disposed within the acoustic enclosure;

an amplifier connected to the speaker the amplifier receiving an anti-noise signal from an acoustic controller; and a port dish disposed adjacent to the acoustic outlet port, the port dish being generally arcuate and extending perpendicularly from a plane defining the acoustic outlet port, the port dish being positioned partially about a circumference of the acoustic outlet port for reducing the impedance mismatch between the acoustic outlet port and an area surrounding the acoustic outlet port.

21. The silencing system according to claim 20, wherein the port dish increases the acoustic coupling between an anti-noise signal radiating from the acoustic outlet port and a noise signal radiating from an exhaust conduit.

22. The silencing system according to claim 20, further comprising a microphone mounted to the housing, the port dish being disposed between the acoustic outlet port and the microphone.

23. The silencing system according to claim 22, wherein said port dish provides a heat shield for the microphone.

24. The silencing system according to claim 20, wherein the housing is mounted to an exhaust conduit.

25. A modular active noise cancellation exhaust silencing unit comprising:

a housing defining an acoustic enclosure having an acoustic outlet port, the housing being detachably mounted to one side of an exhaust conduit;

a speaker disposed within the acoustic enclosure;

a mounting assembly secured to the exhaust conduit, the mounting assembly including a mounting bracket and a band clamp for securing the mounting bracket to the exhaust conduit, the mounting bracket being generally U-shaped and having a first pair of apertures for receiving the band clamp, a second pair of apertures for receiving a fastener, the mounting bracket further including a tap formed in a central portion thereof for receiving a support arm extending from the housing; and at least one corresponding mounting stand-off form on the housing, the mounting stand-off aligning with the second pair of apertures and securing to the mounting bracket with the fastener for supporting the housing on the exhaust conduit.

26. The modular silencing unit according to claim 25, wherein the housing is capable of being mounted on the exhaust conduit in combination with at least one other modular silencing unit.

27. The modular silencing unit according to claim 25, further comprising an amplifier mounted to the housing.

28. The modular silencing unit according to claim 27, further comprising a controller unit mounted to the housing.

29. The modular silencing unit according to claim 28, further comprising a microphone associated with the housing.

30. The modular silencing unit according to claim 25, wherein the housing is a one-piece casting of aluminum which incorporates a speaker mounting plate for mounting the speaker.

31. A modular active noise cancellation exhaust silencing unit, comprising:

a housing defining an acoustic enclosure having an acoustic outlet port, the housing being detachably mounted to one side of an exhaust pipe, the acoustic outlet port being positioned within a plane defined by an opening of the exhaust pipe;

a speaker disposed within the acoustic enclosure;

a microphone mounted to the housing, said microphone being supported by a microphone stand which is mounted to a microphone platform portion of the housing; and a port dish disposed adjacent to the acoustic outlet port, the port dish positioned partially about the circumference of the acoustic outlet port, the port dish extending perpendicularly from a plane of the acoustic outlet port for increasing the acoustic coupling between and anti-noise signal radiating from the acoustic outlet port and a noise signal radiating from the exhaust pipe.

32. The modular silencing unit according to claim 31, further comprising a cap mounted over top of the microphone.

33. The modular silencing unit according to claim 31, wherein the microphone stand includes a plurality of stand portions stacked on top of each other.

34. An active noise cancellation silencing system for attenuating a noise signal radiating from an exhaust conduit comprising:

a modular housing defining an acoustic enclosure, the modular housing including a body portion and a cover portion, the body portion having a first opening defined by a first mating flange, and the cover portion including a second opening defined by a second mating flange, wherein the first and second mating flanges are similarly dimensioned such that the body portion can receive the cover portion for sealing the acoustic enclosure;

a mounting assembly secured to the exhaust conduit, the mounting assembly including a mounting bracket and a band clamp for securing the mounting bracket to the exhaust conduit;

at least one corresponding mounting stand-off formed on the modular housing, the mounting stand-off aligning with and securing to the mounting bracket with a fastener for supporting the modular housing on the exhaust conduit;

an acoustic outlet port formed in the body portion, the modular housing being detachably mounted along the side of the exhaust conduit such that the acoustic outlet port lies within a plane defined by an opening of the exhaust conduit;

a speaker mounted within the acoustic enclosure, the speaker having a radiating face supported by a speaker plate formed within the acoustic enclosure;

a pressure plate disposed against a rear surface of the speaker and an axial force member operably associated with the pressure plate for applying a force between the pressure plate and an inside surface of the body portion for securing the speaker against the speaker plate;

an amplifier mounted within the cover portion and connected to the speaker;

a microphone mounted in proximity to the exhaust pipe;

a port dish disposed adjacent to the acoustic outlet port, the port dish positioned partially about the circumference of the acoustic outlet port, the port dish increasing the acoustic coupling between an anti-noise signal radiating from the acoustic outlet port and a noise signal radiating from the exhaust conduit; and a control unit mounted within the cover portion in communication with the microphone for receiving signals therefrom, the control unit determining an anti-noise signal for the amplifier for creating an amplified anti-noise responsive to a detected noise source.

35. The silencing system of claim 34 wherein the port dish extends perpendicularly from a plane of the acoustic outlet port for reducing the impedance mismatch between the acoustic outlet port and an area surrounding the acoustic outlet port.

* * * * *

UNITED STATES PATENT AND TRADEMARK OFFICE
CERTIFICATE OF CORRECTION

PATENT NO : 6,072,880
DATED : June 6, 2000
INVENTOR(S) : J. Clay Shipps et al

It is certified that error appears in the above-identified patent and that said Letters Patent are hereby corrected as shown below:

Column 14, line 20 (Claim 25), "form" should be --formed--.

Signed and Sealed this

Eighth Day of May, 2001

*Attest:*

NICHOLAS P. GODICI

*Attesting Officer*

*Acting Director of the United States Patent and Trademark Office*